United States Patent [19]

Hammerslag

[11] Patent Number: 5,665,106
[45] Date of Patent: Sep. 9, 1997

[54] VASCULAR PATCH APPLICATOR

[75] Inventor: Julius G. Hammerslag, San Juan Capistrano, Calif.

[73] Assignee: Hemodynamics, Inc., San Clemente, Calif.

[21] Appl. No.: 523,839

[22] Filed: Sep. 7, 1995

Related U.S. Application Data

[62] Division of Ser. No. 314,357, Sep. 28, 1994, which is a continuation of Ser. No. 278,728, Jul. 21, 1994, Pat. No. 5,529,577, which is a continuation of Ser. No. 127,769, Sep. 28, 1993, abandoned.

[51] Int. Cl.$^6$ ................................. A61B 17/00
[52] U.S. Cl. ................... 606/214; 606/213; 606/151; 604/311; 604/285
[58] Field of Search ............... 606/212–214, 606/151, 117, 92–95, 194, 191, 198; 604/96, 98, 310, 311, 11–18, 104, 160, 264, 280, 285, 286, 287, 288; 623/10, 11; 401/263; 602/52, 57

[56] References Cited

U.S. PATENT DOCUMENTS

| | | |
|---|---|---|
| 55,008 | 5/1866 | Gannett. |
| 1,071,063 | 8/1913 | Lee. |
| 1,083,532 | 1/1914 | Grayham. |
| 1,577,465 | 3/1926 | Houge. |
| 2,012,164 | 8/1935 | Grodon. |
| 2,388,321 | 11/1945 | Gereke. |
| 2,626,647 | 2/1953 | Barton. |
| 2,752,920 | 7/1956 | Kurkijian. |
| 3,220,413 | 11/1965 | Sunnen. |
| 3,223,083 | 12/1965 | Cobey. |
| 3,527,841 | 9/1970 | Wicker, Jr. et al.. |
| 3,559,652 | 2/1971 | Banitt et al.. |
| 3,577,516 | 5/1971 | Gould et al.. |
| 3,772,599 | 11/1973 | Ernst et al.. |
| 4,243,035 | 1/1981 | Barrett ............................ 604/181 |
| 4,449,645 | 5/1984 | Korwin et al. ..................... 604/224 |
| 4,545,374 | 10/1985 | Jacobson. |
| 4,560,352 | 12/1985 | Neimeister et al. ............... 604/224 |
| 4,578,055 | 3/1986 | Fischer. |
| 4,900,303 | 2/1990 | Lemelson ........................ 604/285 |
| 4,981,483 | 1/1991 | Akimova et al.. |
| 4,993,948 | 2/1991 | Cameron et al.. |
| 5,011,493 | 4/1991 | Belykh et al.. |
| 5,021,059 | 6/1991 | Kensey et al.. |
| 5,156,613 | 10/1992 | Sawyer. |
| 5,158,543 | 10/1992 | Lazarus. |
| 5,201,712 | 4/1993 | Bryant. |
| 5,209,776 | 5/1993 | Bass et al.. |
| 5,222,939 | 6/1993 | Tiefenbrun. |
| 5,236,455 | 8/1993 | Wilk et al.. |

(List continued on next page.)

FOREIGN PATENT DOCUMENTS

| | | |
|---|---|---|
| WO/9107136 | 5/1991 | WIPO. |
| WO/9221297 | 12/1992 | WIPO. |
| WO/9306878 | 4/1993 | WIPO. |
| WO/9308746 | 5/1993 | WIPO. |

OTHER PUBLICATIONS

Long Term Pathological Follow–up of Cerebral Arteriovenous Malformations Treated by Embolization with Bucrylate, By Harry V. Vinters et al., The New England Journal of Medicine, Feb. 29, 1986 pp. 477–483.

*Primary Examiner*—Jeffrey A. Schmidt
*Attorney, Agent, or Firm*—Knobbe, Martens, Olson & Bear, LLP

[57] ABSTRACT

Disclosed is a device for delivering tissue adhesives and/or sealant patches to a surface which covers or surrounds a lumen, cavity or organ, or potential lumen or cavity, within a human or other animal. Also disclosed is a method of delivering tissue adhesives and/or sealant patches to a surface which covers or surrounds a lumen, cavity or organ, or potential lumen or cavity. The method is particularly suited to sealing perforations in vascular walls, such as after arterial access for Percutaneous Transluminal Coronary Angioplasty (PTCA), Percutaneous Coronary Angiography and Percutaneous Coronary Atherectomy and similar diagnostic and therapeutic procedures.

10 Claims, 7 Drawing Sheets

U.S. PATENT DOCUMENTS

| | | |
|---|---|---|
| 5,292,333 | 3/1994 | Johnson . |
| 5,312,355 | 5/1994 | Lee . |
| 5,324,305 | 6/1994 | Kanner . |
| 5,383,477 | 1/1995 | De Matteis .............................. 606/213 |
| 5,383,896 | 1/1995 | Gershony et al. . |
| 5,383,897 | 1/1995 | Wholey . |
| 5,391,183 | 2/1995 | Janzen et al. . |
| 5,395,383 | 3/1995 | Adams et al. . |
| 5,397,311 | 3/1995 | Walker et al. . |
| 5,431,639 | 7/1995 | Shaw . |
| 5,443,481 | 8/1995 | Lee ........................................... 606/213 |
| 5,456,720 | 10/1995 | Schultz et al. .......................... 606/213 |

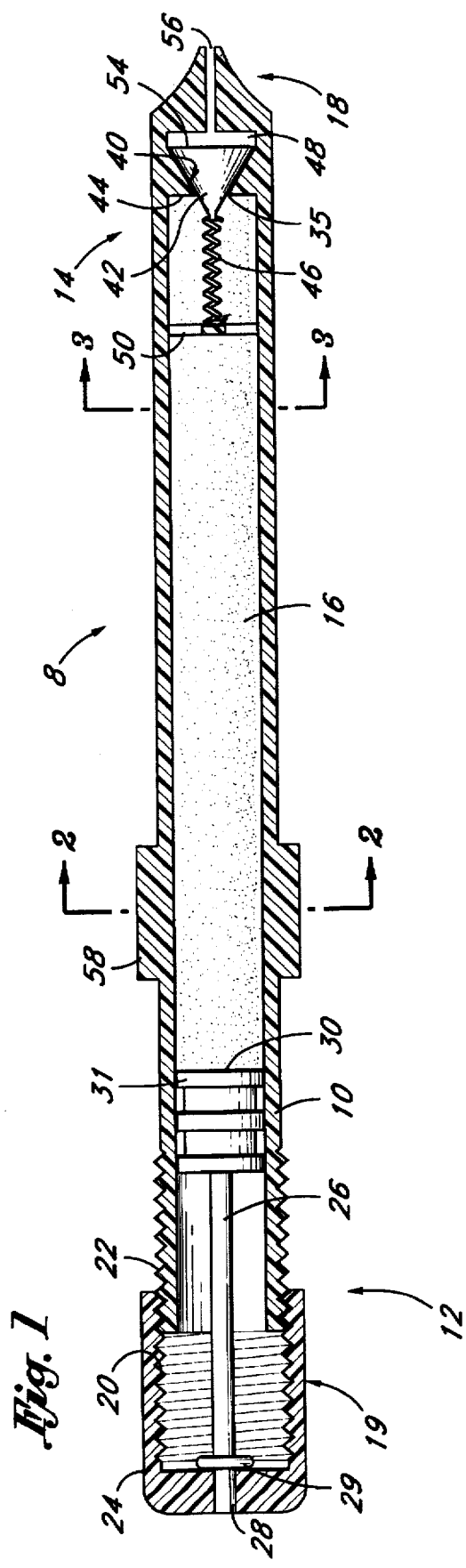
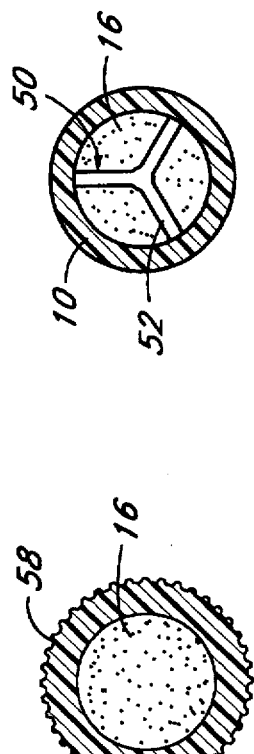

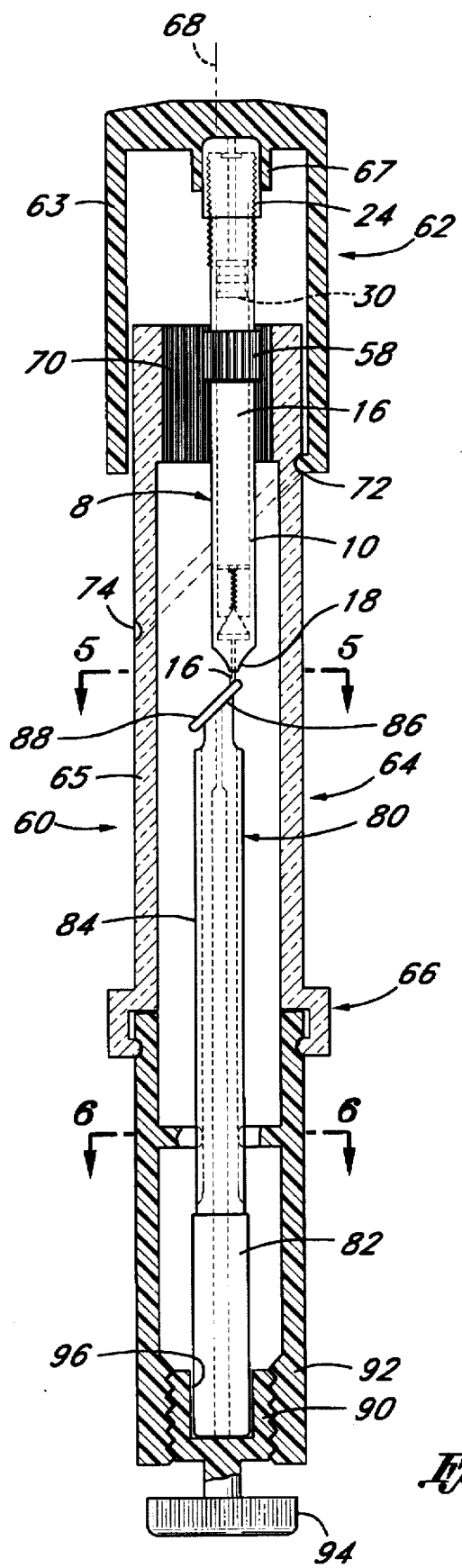
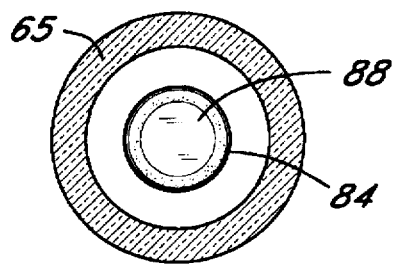
Fig. 5
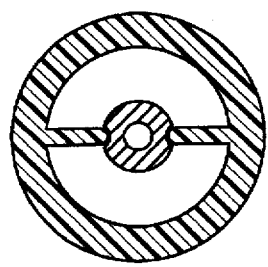
Fig. 6
Fig. 4

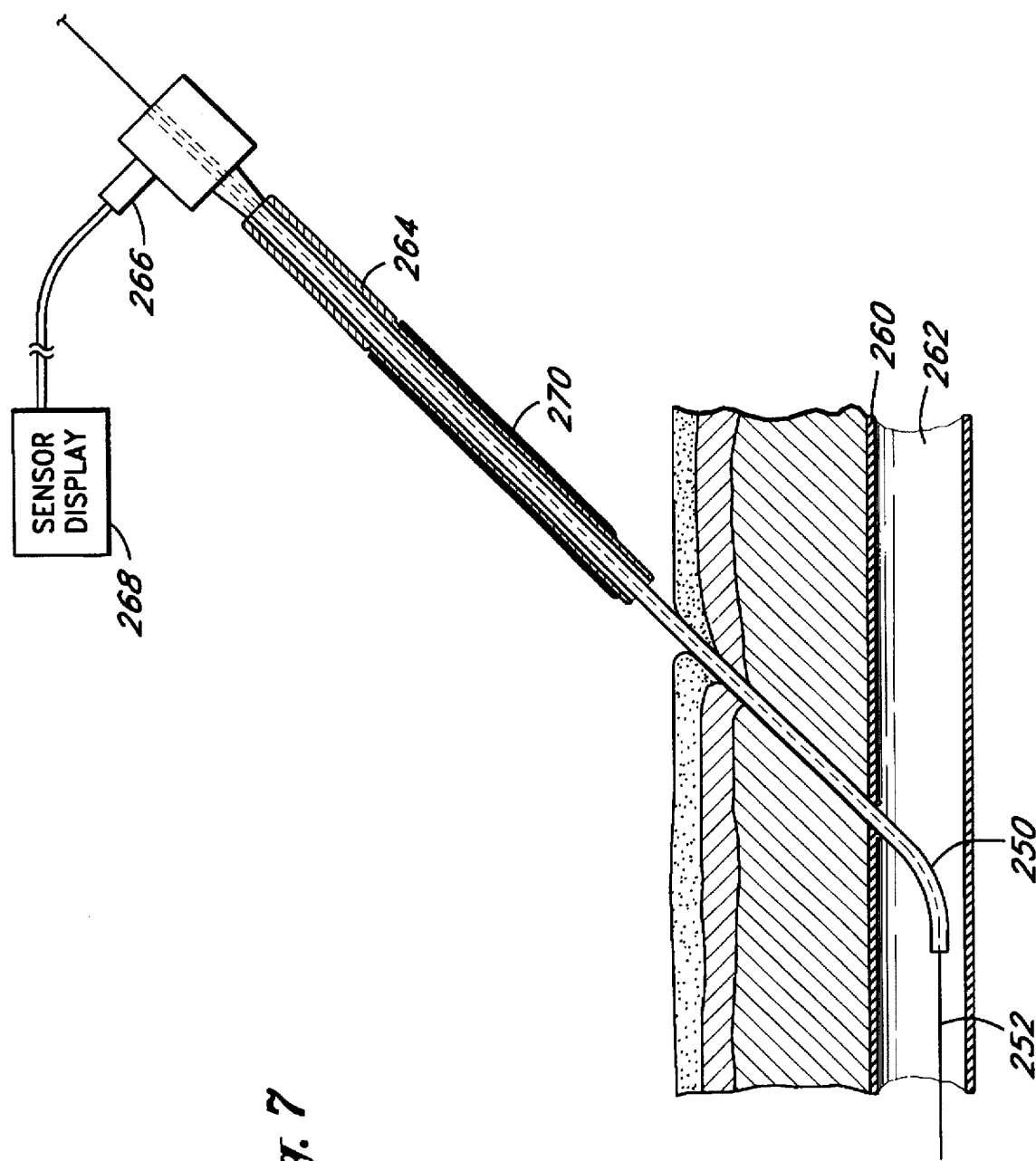

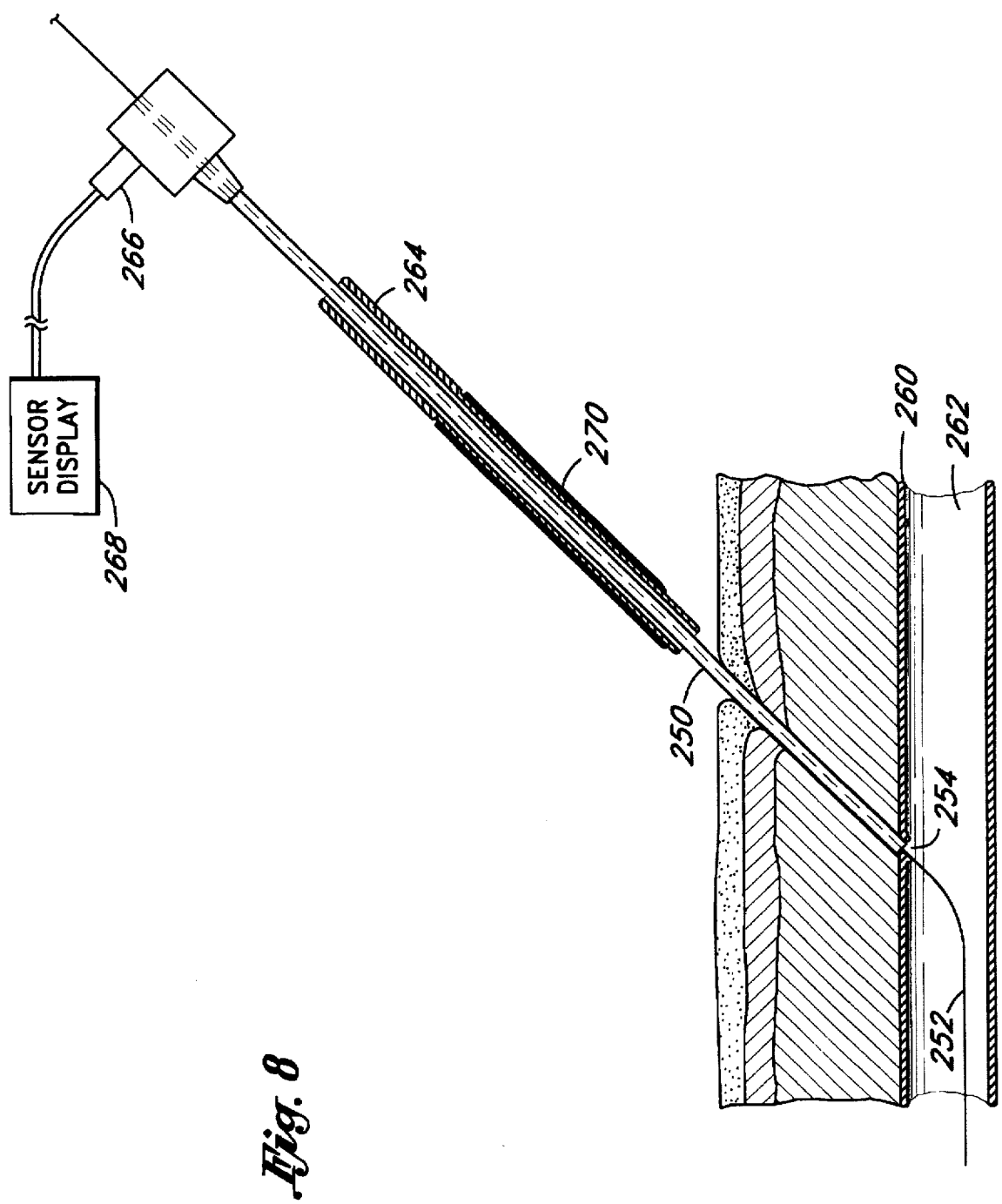

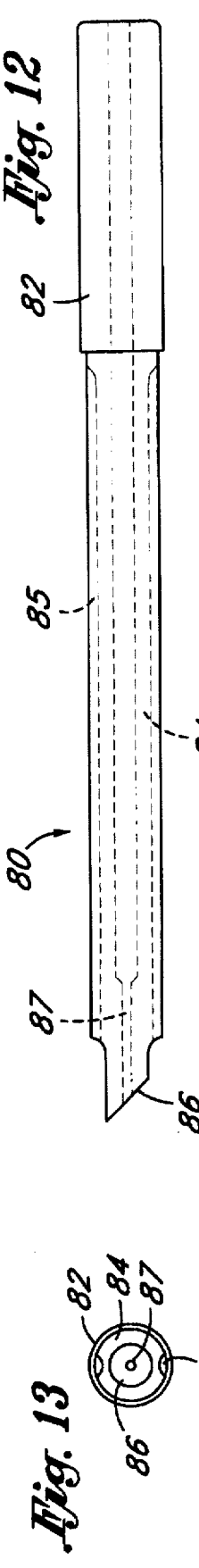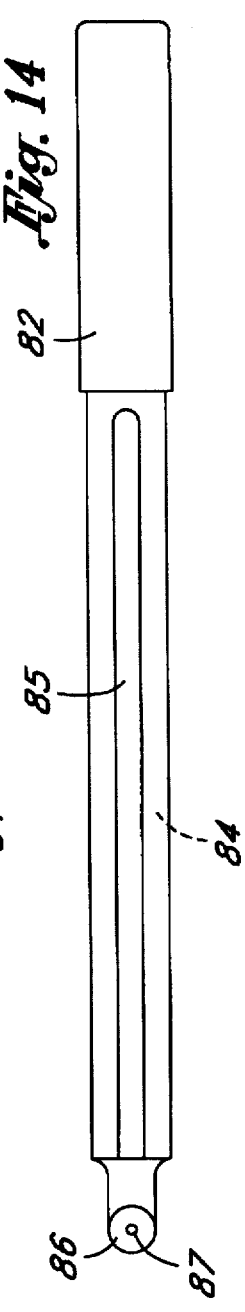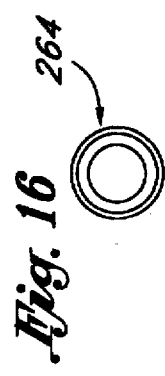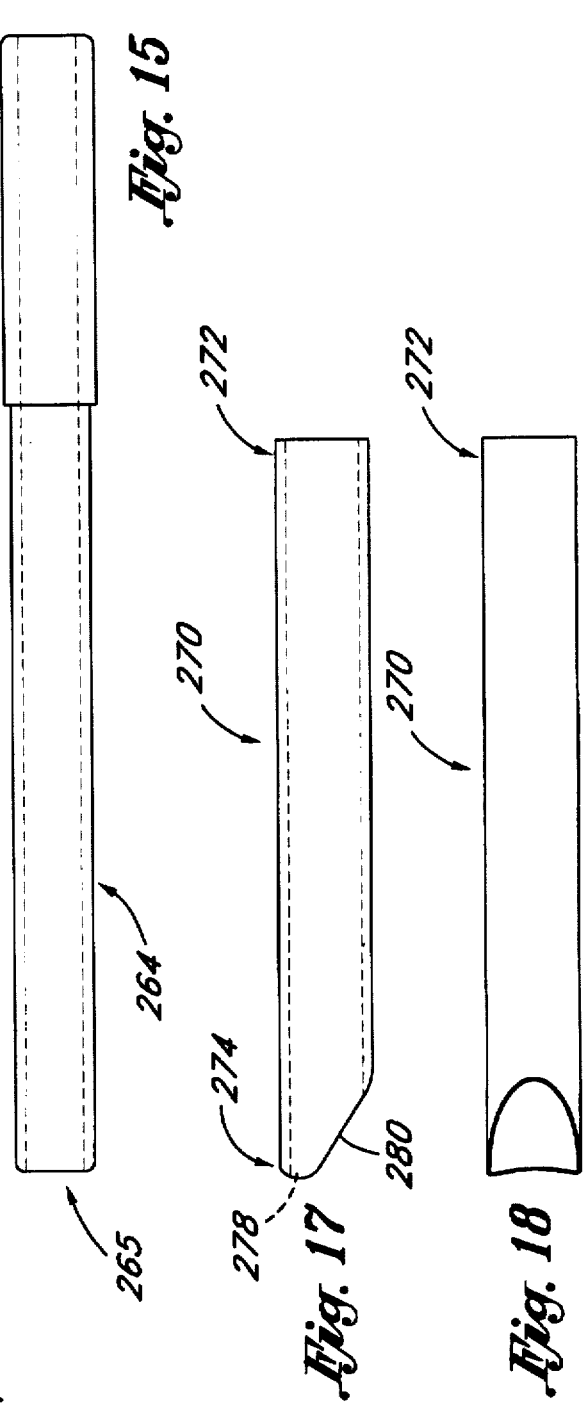

5,665,106

VASCULAR PATCH APPLICATOR

RELATED CASE

This application is a division of U.S. patent application Ser. No. 08/314,357, filed Sep. 28, 1994, which is a continuation of U.S. patent application Ser. No. 08/278,728, filed Jul. 21, 1994, now U.S. Pat. No. 5,529,577 which is a file wrapper continuation of U.S. patent application Ser. No. 08/127,769, filed Sep. 28, 1993 now abandoned.

BACKGROUND ON THE INVENTION

1. Field of the Invention

This invention relates to a method and an associated device for sealing a puncture in a vessel within mammals. In particular, the invention relates to a method and an associated device for delivering a sealant patch and/or tissue adhesive to seal a puncture in a vessel.

2. Description of Related Art

Percutaneously accessing major vascular structures is a key step in a variety of diagnostic and therapeutic procedures, including Percutaneous Transluminal Coronary Angioplasty (PTCA), Percutaneous Corona Angiography and Percutaneous Corona Atherectomy. After the procedure is completed, the instruments used to perform the procedure are withdrawn from the vessel leaving a potential source of bleeding.

The most common method used to prevent post-procedure bleeding at the access site involves the application of direct pressure to the perforation site until normal physiologic pathways have sealed the access site. There are several problems with this method. First, the pressure application technique may fail to prevent hemorrhage. Such a hemorrhage may be life-threatening hemorrhage or lead to a large hematoma. A large hematoma in the groin, for instance, may compromise the major nerve supply to the anterior lower extremity.

Secondly, the pressure application technique extends the length of the in-hospital stay. For example, a PTCA may be completed in 2 to 3 hours, but the patient will typically be hospitalized for several additional hours or overnight, simply to allow the access site to seal physiologically. During this extended hospital stay the patient is required to stay immobile, often with a sand bag taped to his thigh (in the case of femoral artery access).

These complication are exacerbated where PTCA procedures are performed in elderly patients which commonly have arteries with reduced natural elasticity. The access perforation in a relatively inelastic artery does not contract or shrink upon itself to the same extent that would occur with an artery of normal elasticity. The resulting undeflected perforation in a relatively inelastic artery typically is two to three times larger than an access perforation in a normal artery, further complicating the initiation of hemostasis and the normal physiologic sealing of the access site.

More than 500,000 PTCAs were performed worldwide in 1992 (Cowen Report, March 1993), as well as several times that number of other procedures requiring accessing major vascular structures percutaneously. Thus, the increased length of in-hospital stay necessitated by the pressure application technique considerably increases the expense of procedures requiring such vascular access.

A technique that would allow faster and safer sealing of a vascular access site would save a significant amount of health care resources. There remains a need for such a technique.

SUMMARY OF THE INVENTION

There is provided in accordance with one aspect of the present invention, a method of closing a vascular perforation of the type produced during a percutaneous transluminal catheterization procedure. The method comprises the steps of providing an adhesive patch applicator kit of the type having a housing, an adhesive applicator therein, a patch applicator therein, and an adhesive patch. A first portion of the housing is manipulated with respect to the second portion of the housing to express a quantity of adhesive from the reservoir onto the patch. Thereafter, the applicator having the patch thereon is removed from the housing and advanced percutaneously to position the patch against the vascular perforation. The applicator is thereafter removed while leaving the patch adhered to the vascular perforation.

In accordance with another aspect of the present invention, there is provided an adhesive patch applicator kit. The kit comprises a housing having a rotatable cap and a chamber therein, said cap rotatable about a longitudinal axis.

A patch applicator within the chamber is removably connected to one of the housing or the rotatable cap. A reservoir is also provided in the chamber, said reservoir connected to the other of the housing and the cap.

A tip on the reservoir is provided for expressing adhesive, and an adhesive patch is removably attached to the applicator such that rotation of the cap about the longitudinal axis relative to the housing expresses adhesive from the reservoir through the tip and onto the patch.

In accordance with a further aspect of the present invention, there is provided a method for patching a vascular puncture. The method comprises providing a patch applicator of the type having a proximal handle portion, an intermediate extender portion, and a distal patch contact surface.

A vascular patch is releasably secured to the contact surface, and a quantity of tissue adhesive is applied to the distal surface of the patch. The applicator is thereafter percutaneously advanced to contact the patch to the vascular perforation site. The applicator is thereafter removed, leaving the patch secured to the vessel wall at the perforation site.

Further features and advantages of the present invention will become apparent to those of ordinary skill in the art in view of the following disclosure when considered together with the attached drawings and claims.

BRIEF DESCRIPTION OF THE DRAWINGS

FIG. 1 is a side elevational cross-sectional view of an adhesive applicator in accordance with one aspect of the present invention.

FIG. 2 is a cross-sectional view taken along the line 2—2 of FIG. 1.

FIG. 3 is a cross-sectional view taken along the line 3—3 of FIG. 1.

FIG. 4 is a cross-sectional elevational view of an applicator kit in accordance with the present invention.

FIG. 5 is a cross-sectional view taken along the line 5—5 in FIG. 4.

FIG. 6 is a cross-sectional view taken along the line 6—6 in FIG. 4.

FIG. 7 is a schematic representation of a catheter introduction sheath having expander and introducer cannulas thereon, in position within a vessel.

FIG. 8 is a schematic representation as in FIG. 7, with the catheter introduction sheath withdrawn from the artery.

FIG. 12 is a side elevational view of a vascular patch applicator in accordance with the present invention.

FIG. 13 is a left end view of the patch applicator of FIG. 12.

FIG. 14 is a bottom plan view of the patch applicator of FIG. 12.

FIG. 15 is a side elevational view of an expander cannula in accordance with the present invention.

FIG. 16 is a left end view of the expander of FIG. 15.

FIG. 17 is a side elevational view of an introducer cannula in accordance with the present invention.

FIG. 18 is a bottom plan view of the introducer of FIG. 17.

DETAILED DESCRIPTION OF PREFERRED EMBODIMENTS

Figure 9:
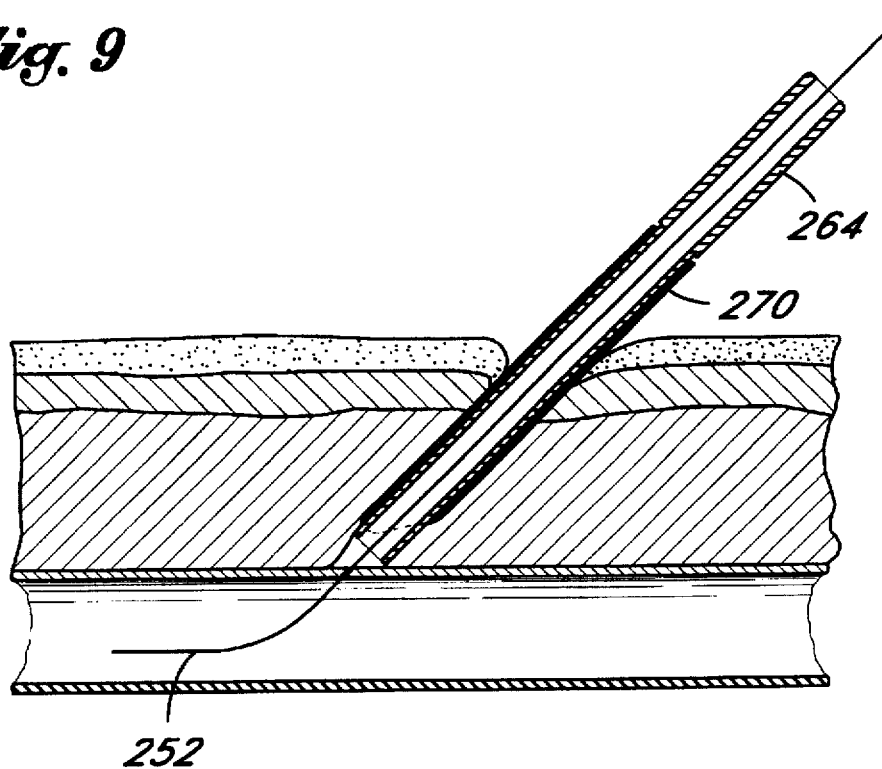
FIG. 9 is a schematic representation as in FIG. 8, with the introducer and expander positioned against the artery wall, and the catheter introduction sheath removed.

As discussed above, there is a need for a technique which will seal a vascular perforation created during a variety of commonly performed diagnostic and therapeutic procedures, including for example, Percutaneous Transluminal Coronary Angioplasty (PTCA), Percutaneous Coronary Angiography and Percutaneous Coronary Atherectomy. In addition, the device and method may have applications in the emergency treatment of trauma, wound closure following surgical procedures and the like. For convenience, the present disclosure will consider primarily the vascular perforation application.

An ideal technique would seal the perforation rapidly, cost effectively and permanently. If used to close a femoral or brachial artery, the technique should result in a seal that can withstand the uppermost potential limits of systolic blood pressure (around 300 mmHg) found in those vessels and the seal should be put in place with an absence of or no more than minimal enlargement of the original percutaneous entrance. One aspect of the present invention addresses the problems inherent in closing a perforation of a vessel, such as, for example, in a femoral or brachial artery following coronary artery or other vessel catheterization by providing a device, and a method that can be used to create a rapid and permanent seal.

The Adhesive Applicator

Referring to FIG. 1, there is illustrated one embodiment of the adhesive applicator for delivering a tissue adhesive to the surface of a vascular patch. For convenience, tissue adhesive will be discussed herein, although any of a wide variety of other fluids or fluid-like media can be delivered utilizing the reservoir of the present invention. The apparatus of the present invention can also be utilized to deliver materials to any of a wide variety of structures, as will be apparent to one of skill in the art. The present disclosure will discuss embodiments primarily intended for delivery to patches or to tissue of the type which covers or surrounds a lumen, cavity or organ, or potential lumen or cavity, within a human or other animal.

The illustrated embodiment comprises an applicator 8 having a generally tubular housing 10 with a proximal control end 12, a distal delivery end 14 and a reservoir 16. The distal delivery and 14 is preferably provided with a delivery tip 18 for guiding the adhesive expressed from reservoir 16, as will become apparent in view of the disclosure below.

A control 19 is provided near proximal end 12 for controllably expressing adhesive from the reservoir 16, as will be discussed. Any of a variety of control structures can be used, such as push buttons, levers, plungers, movable walls and the like. Preferably, a control in the form of a rotating knob is provided, such that rotation of the knob causes a measured amount of adhesive to be expressed from the tip 18 as will be discussed. Other types of controls will be apparent to one of skill in the art in view of the disclosure herein.

In the illustrated embodiment, the control 19 comprises a threaded surface 20 for engaging a corresponding threaded surface 22 on the tubular housing 10. Threaded surface 20 is conveniently provided on the radially interior surface of a tubular end cap 24. End cap 24 is linked to movable wall 30 such as by way of a rod 26.

In the foregoing embodiment, the cap 24 can be rotated with respect to tubular body 10 to produce an axial distal travel of the cap 24 with respect to the tubular body 10. Rod 26 causes the movable wall 30 to advance distally a corresponding distance, thereby expressing adhesive from the reservoir 16

Preferably, either the proximal or distal ends of rod 26 are rotatably secured to the movable wall 30 or cap 24 so that the cap 24 can be freely rotated without causing a rotation of annular seal 31 with respect to the interior wall of tubular body 10. In the illustrated embodiment, the proximal end of rod 26 is rotatably received within an aperture 28 in the cap 24. A stop 29 is provided to limit proximal axial travel of rod 26 with respect to cap 24. Any of a wide variety of equivalent structures for accomplishing the objectives of the control 19 can be readily envisioned by one of ordinary skill in the art in view of the disclosure herein.

Manipulation of the control 19 advances the moveable wall 30 in a manner that reduces the volume of the reservoir 16, thereby expressing contents from the reservoir by way of distal tip 18 as discussed below. The moveable wall 30 may comprise a moveable diaphragm, other flexible wall, slidable piston, or other structure for expressing contents from reservoir 16 in response to manipulation of control 19. For instance, as illustrated in FIG. 1, the moveable wall 30 is the distal face of a slidable piston 32 or plunger with a plurality of annular seals 31 which prevent undesired proximal flow of adhesive from the reservoir 16.

The reservoir 16 contains any of a variety of tissue adhesives. Suitable adhesives for in vivo use include adhesives within the cyanoacrylate family. In one embodiment, the tissue adhesive comprises one or more of methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl-2-cyanoacrylate, alkoxyalkyl 2-cyanoacrylates or fluorinated 2-cyanoacrylates or combinations, thereof. Biocompatibility for particular applications can be determined from the literature or through routine experimentation.

Preferably, the tissue adhesive comprises ethyl cyanoacrylate or butyl-2-cyanoacrylate. These latter two compounds, available from Loctite Corporation (Hartford, Conn.), are normally in a liquid state with water-like viscosity. They harden almost instantaneously upon exposure to atmospheric humidity. Therefore, the reservoir 16 is provided with moisture-tight proximal and distal ends formed by the moveable wall 30 and the valve 42 to maintain the tissue adhesive in liquid state prior to expression. Preferably, the device is also produced under low humidity conditions and stored in a desiccated package. A removable distal cap (not illustrated) may also be used.

Cyanoacrylate adhesives have been found to harden relatively rapidly when stored below a critical volume of adhesive. Hence, if cyanoacrylate is used, it will be preferable for the reservoir 16 to contain more adhesive than is necessary to seal a typical vascular access site. Preferably, a reservoir volume of at least about 1 to 2 gm is provided to maintain the cyanoacrylate in liquid form in the applicator prior to use. The total volume of adhesive, the desiccation measures and sealing structures on the reservoir 16 can be optimized to produce a desired shelf life by one of skill in the art in view of the disclosure herein.

When used to seal an in vivo tissue surface, cyanoacrylates have several particular advantages. First, they harden almost instantaneously on contact, because of the moisture content of most tissues. For example, they will harden when placed on living vascular walls, and endothelial and mesothelial surfaces. Second, experiments by the inventor indicate that cyanoacrylate sealed vascular punctures can withstand several times the maximum potential systolic pressure, and hence, would not be expected to fail when used to seal a perforation on a vascular wall. Also, cyanoacrylates are naturally thrombogenic. This is an advantage in sealing vascular walls as it promotes the first step in healing the wall. Further, because it seals so rapidly, the risk of embolization or migration can be minimized through the use of the applicators disclosed herein.

Various compounds may be added to the cyanoacrylates to alter the properties of the adhesive. For example, polyacrylic acid having a molecular weight of 200,000 to 600,000 may be cross-linked to the cyanoacrylate to form a suitable biocompatible material. These combination compounds allow the absorbability and resorption rate to be coordinated with the tissue regeneration rate and feature higher elasticity than cyanoacrylates alone. Other additives, such as stabilizers, viscosity modifiers and medications can also be included as desired.

In a preferred embodiment of the present invention, the cyanoacrylate is mixed with a thickening agent to optimize the viscosity. In one embodiment, cyanoacrylate liquid is mixed with Cabosil™ (available from Cabot Manufacturing) to produce a relatively viscous cyanoacrylate gel. When the gel is expressed from the applicator 8 onto the vascular patch, it generally maintains its form as an annular bead without soaking into the patch.

Upon immersion of the patch in a body fluid such as blood, the inventor has determined that only an outer layer of the cyanoacrylate gel hardens to form a protective skin. As the vascular patch is thereafter pressed against the vessel wall, the pressure ruptures the cyanoacrylate gel skin, to release fresh cyanoacrylate and bond the patch to the vascular wall. The ability to transport uncured cyanoacrylate, within an outer cured skin, through an aqueous environment enables use of the present invention without the need to rigorously dry the access pathway for application of the vascular patch.

The distal delivery end 14 of the applicator 8 is provided with an annular valve seat 40 which cooperates with a valve 42. The valve seat 40 includes a proximal wall 44 which defines an aperture 35 that opens into the reservoir 16. The aperture 35 has a diameter smaller than that of the reservoir 16 as defined by the tubular housing 10. The valve seat 40 comprises a sealing surface which preferably tapers radially outwardly in the distal direction, from the aperture 35 towards the wall of the tubular housing 10. The sealing surface thus defines generally a frusto-conical shape which mates with a correspondingly shaped surface of the valve 42, as discussed below.

The valve 42 desirably is normally closed. That is, the valve 42 is preferably biased against the valve seat 40. Any of a variety of biasing structures can be used, such as, for example, springs, diaphragms, magnets, resilient polymeric materials, and the like. In the illustrated embodiment, a helical spring 46 biases the valve 42 in the proximal direction against the valve seat 40.

In one embodiment, a distal end of the spring 46 passes through a transverse aperture of the valve proximal end. The spring 46, however, may be attached to the valve 42 by any of a variety of other means known in the art as well.

The tubular housing 10 includes structure which supports a proximal end of the spring 46. In the illustrated embodiment, the tubular housing 10 includes a spider structure 50 which extends within the tubular housing 10. As best illustrated in FIG. 3, the spider structure 50 includes a plurality of legs 52, preferably three legs, which extend from the wall of the housing 10 to the center of the reservoir 16. The proximal end of the spring 46 is attached to the spider structure 50 in a conventional manner. Alternatively, proximal end of spring 46 is secured directly to the inner surface of the housing 10 such as by a rivet, penetration through the wall, or spot weld, depending upon the construction material of the housing 10.

Activation of the control 19 advances the plunger 30 in the distal direction to increase the adhesive pressure within the reservoir 16. Once the produced pressure within the reservoir 16 exceeds the biasing force exerted by spring 46 on the valve 35, the valve 35 opens to express adhesive past the valve 42 and the valve seat 44.

In the illustrated embodiment, a space 48 is provided in the distal tip 18 to permit axial distal displacement of valve 42. Adhesive expressed past the valve 42 escapes around the radially outermost extent 54 of the valve 42 and into the space 48. Adhesive is thereafter conducted from the space 48 by way of a lumen 56 out of the distal end of delivery tip 18.

Referring to FIGS. 1 and 2, the housing 10 is further provided with an annular gear 58 to cooperate with annular gear 70 discussed infra. Gear 58 facilitates rotation of the housing 10 with respect to the end cap 24 to permit expression of adhesive by way of lumen 56.

Applicator Housing

Referring to FIGS. 4–6, there is disclosed an applicator housing 60 in accordance with the present invention. The housing 60 together with an adhesive reservoir and an adhesive patch applicator form a kit for preparing and applying a patch to a vascular wall. The kit illustrated in FIG. 4 is automated to deliver a predetermined volume of adhesive to a preselected pattern or path along the vascular patch. In an alternative embodiment, the kit may simply include the basic components of an adhesive reservoir, a patch and a patch applicator, so that the adhesive can be manually applied to the patch by medical personnel.

The housing 60 generally comprises a relatively rotatably component 62 and a relatively nonrotatable component 64. The rotatable component can be generally in the form of a cap 63, and the nonrotatable component can be generally in the form of a tubular body 65. A releasable connection 66 is further provided, to enable opening the housing 60 to remove the contents thereof.

The main components of housing 60 may be produced in accordance with any of a variety of techniques known in the art, such as machining metal components or using any of a variety of known forming techniques for plastic components. Preferably, the housing 60 comprises injection molded or extruded and fabricated plastic components. The plastic is preferably any of a variety of medical grade, sterilizable plastics, such as high density polyethylene, and others well known in the art. Preferably, at least a portion of the housing is transparent, to permit visual observation of the adhesive application process.

In general, the housing 60 provides a vehicle for applying a predetermined amount of tissue adhesive to the surface of a vascular patch which has been previously releasably connected to a patch applicator, so that the vascular patch is ready for application to the wall of a perforated vessel.

The housing 60 generally is provided with a tissue adhesive applicator of the type containing a reservoir of tissue adhesive. In the illustrated embodiment, the tissue adhesive applicator 8 is the same as that illustrated in FIG. 1. Thus, the applicator 8 is provided with a generally tubular body 10, which is rotatable relative to an end cap 24. Rotation of tubular body 10 with respect to end cap 24 causes relative axial motion of tubular body 10 with respect to end cap 24, thereby advancing a movable wall 30 into adhesive reservoir 16 as has been discussed.

The cap 63 is rotatable about a longitudinal axis 68, which, in a preferred embodiment, coincides with the longitudinal axis of the tubular body 65. End cap 24 is secured to the interior end wall of rotatable cap 63, such that the longitudinal axis of rotation of tubular body 10 is offset radially from longitudinal axis 68. In this manner, rotation of cap 63 about its longitudinal axis 68 causes the distal tip 18 of housing 10 to travel in a circle about longitudinal axis 68

End cap 24 can be secured to the interior end wall of cap 63 in any of a variety of ways known in the art, such as by adhesives, thermal or solvent bonding, and the like. In the illustrated embodiment, end cap 24 is positioned within an axially extending annular flange 67 which was integrally molded with cap 63.

The interior wall of housing 64 is provided with a radially inwardly directed annular ring of axially extending gear teeth 70 adapted for engaging the gear 58 on the housing 10. Tissue adhesive expression is accomplished by rotating the cap 63 with respect to the tubular body 65 such that gear 58 engages gear 70 and the tubular body 10 is thereby rotated with respect to end cap 24.

The cap 63 is further provided with a radially inwardly extending tab 72 which engages an annular slot 74 on the outer wall of tubular body 65. Annular slot 74 lies in a plane which is inclined with respect to a perpendicular through longitudinal axis 68, so that rotation of cap 63 causes a reciprocal axial travel of cap 63 with respect to the housing 65. For this purpose, the gear teeth 70 on the interior wall of housing 64 are provided with a sufficient axial length that the gear 58 remains engaged with gear teeth 70 throughout the range of axial travel produced as tab 72 rides in annular recess 74.

Patch Applicator

The apparatus 60 is further provided with a patch applicator 80 for transporting a vascular patch having adhesive thereon to a treatment site in a patient. In general, applicator 80 comprises a proximal handle portion 82, and an extender portion 84. The extender portion 84 terminates at its distal end at an inclined patch contact surface 86. In the illustrated embodiment, a patch 88 is shown on the patch surface 86. The patch applicator is shown in greater detail in FIGS. 11–14.

In the illustrated embodiment, the patch applicator 80 has an overall length within the range of from about 5 cm to about 15 cm and preferably and length of about 10 cm. The length and other dimensions of the patch applicator 80 can be varied widely to suit the intended use application, and the particular dimensions disclosed herein relate to an embodiment of the patch applicator intended for use in connection with the puncture of a femoral artery in a normal size and weight adult human.

The patch applicator 80 generally comprises a handle portion 82. Handle portion 82 is preferably provided with a slightly larger exterior diameter than the extender portion 84, and may also be provided with friction enhancing structures such as a knurled surface, or other structures known in the art to facilitate gripping by the medical personnel. In the illustrated embodiment, the handle portion 82 has a length of about 3 cm, and a diameter of about 1 cm.

The extender portion 84 is generally in the form of an elongate cylindrical shaft, for advancing through a tissue expanding cannula as will be discussed. The extender portion 84 in the illustrated embodiment has a length of about 7 cm, and a diameter of about ¼". Typically, the diameter of the extender portion 84 and the interior diameter of the tissue expander 270 are compatible so that the extender portion 84 substantially fills the interior of tissue expander 270, but is axially slidably received therein. One or more axially extending channels 85 is preferably provided in the extender portion 84 to provide an axial flow path for body fluids such as blood, so that introduction of the patch applicator into the tissue expander will not operate to pump fluids back through a perforation and into the artery.

Preferably, the patch applicator 80 is additionally provided with a guidewire lumen 87 extending axially therethrough. In the preferred method of the present invention, the patch applicator 80 is advanced towards the vascular perforation along a guidewire, to ensure that the patch will be centered over the vascular perforation. The present inventor has determined that, although the patch applicator system of the present invention can be utilized in the absence of a guidewire, the risk of missing or only partially covering the perforation is increased due to the possibility of migration of the distal end of the tissue expander 270 with respect to the vascular perforation in the absence of a guidewire.

Referring to FIG. 4, the patch surface 86 and distal tip 18 of the adhesive applicator are oriented within the housing 60 such that rotation of the cap 63 simultaneously expresses adhesive onto the patch 88 and travels in a circular path to produce an annular bead of adhesive on the patch 88. Due to the typical entrance angle of the percutaneous puncture frequently utilized in catheterization procedures, as will be discussed, the patch surface 86 is preferably inclined at an angle with respect to a perpendicular to the longitudinal axis 68. Preferably, the patch surface 86 is inclined with the range of from about 20° to about 50° with respect to that perpendicular. Most preferably, the angle is about 30°. The angle of incline of the surface 86 corresponds to the angle of incline of the plane which contains annular recess 74, as illustrated. In this manner, the adhesive applicator tip 18 will travel at a preset distance from the patch 88 throughout the rotational travel of the cap 63.

In a typical embodiment, as illustrated in FIG. 4, a gap is provided between the distal end of delivery tip 18 and the patch 88. This facilitates the flow of a bead of adhesive gel 19 into an annular path around patch 88 However, the gap may create some difficulty and/or irregularities in the size of the bead at the point of initiating adhesive flow. For this purpose, a threaded plug 90 is provided at the proximal end of the applicator 80, for threaded engagement with the wall 92 of tubular body 65. A knurled knob 94 or other gripping structure may be provided, to facilitate rotation of the plug 90 with respect to the wall 92. Plug 90 is further provided with a recess 96 for removably receiving the handle 82 of patch applicator 80

In use, the cap 63 is initially rotated through a fraction of a rotation to develop a bead of adhesive 19 at delivery tip 18. The knob 94 is thereafter rotated to axially advance the patch 88 into contact with the bead of adhesive 19. Once contact has been established, the knob 94 can be rotated in a reverse direction, to stretch out the bead of adhesive 19. Thereafter, the cap 63 is rotated through one full revolution, to produce an annular bead of adhesive gel on the patch 88.

The patch 88 desirably has a size larger than the perforation of the vessel (e.g., an artery) and may have any of a variety of shapes depending upon the application of the patch 88. The patch 88 generally has a circular or oval shape of sufficient dimensions to completely cover the perforation. It is understood, however, that the size of the patch 88 may only cover a portion of the perforation, yet extend across the perforation such as in the form of a strip so as to attach to the surfaces of the vessel on either side of the perforation. The patch 88 preferably has a diameter of at least about 2 mm and preferably at least about 4 mm for applications with a PTCA arterial perforation formed in an inelastic artery.

The patch 88 in one embodiment is porous so tissue adhesive can flow through the pores of the patch 88 to attach the patch 88 to the surface adjacent the perforation and to seal the portion of the patch 88 extending across the perforation. In an exemplary embodiment, the pores have a size of about 300 microns, although it is understood that the pores could have a size ranging between 100µ to 500µ, and more preferably ranging between 200µ to 400µ.

The foregoing embodiment of patch 88 is preferably formed of a mesh, weave or knitted material which is biocompatible, and preferably is biodegradable (i.e., is absorbable within the body). The patch 88 can be formed of any of a wide variety of suitable materials, such as, for example, polytetrafluoroethylene (PTFE), oxidized regenerated cellulose, GELFILM™ available from the Upjohn Co., and collagen. A suitable material from which to form the patch 88 is a sterile absorbable mesh material (either knitted or woven) available commercially as VICRYL™ from Ethicon (a Johnson and Johnson company) of Somerville, N.J.

In a particularly preferred embodiment, the patch comprises a layer of a biocompatible material such as GELFILM™ available from the UpJohn Company. GELFILM patches cut or stamped from sheet stock having a thickness in the area of from about 0.003 to about 0.004 inches have been found to be particularly suited for the purpose of the present invention. However, other thicknesses can be readily used. Thickness and other patch dimensions can be optimized through routine experimentation by one of ordinary skill in the art, in view of the particular material selected for use as the patch.

In another embodiment of the patch, a GELFILM first layer is provided with a second layer comprising collagen. The collagen layer is disposed adjacent the patch surface 86 on applicator 80, and the cyanoacrylate gel or other adhesive is applied to the GELFILM layer. As discussed below in connection with the method of the present invention, the patch preferably has a guidewire aperture therein. In embodiments having a guidewire aperture in the form of a cylindrical puncture extending straight through the center of the patch, the upper collagen layer has been found to facilitate closure of the guidewire hole in the patch due to the tendency of collagen to swell in an aqueous environment.

In an alternate embodiment of the patch of the present invention, the guidewire hole is replaced by a slit in the material of the patch. The slit may be a single linear slit, or two perpendicular slits oriented such as a plus symbol. The slit embodiment permits guidewire installation but tends to be self-closing following removal of the guidewire.

In use, the medical personnel will be required to thread the patch 88 and applicator 80 over the proximal end of a guidewire in position in the patient. To facilitate location of the guidewire opening in the patch, the present inventor has found it convenient to elevate one side of the slit above the plane of the patch while reducing the other side of the slit below the plane of the patch. This can be accomplished by extending a guidewire or mandrel through the slit in the patch, and then laying the guidewire against the patch so that it is generally parallel to the patch but perpendicular to the slit. If this is accomplished while the patch is somewhat moistened, and the guidewire is left in place while the patch dries, the dried patch will tend to retain its modified configuration.

The ability to conform a GELFILM™ patch while it is moist and retain the memory in the dried patch is also desirable in connection with another embodiment of the applicator 80 of the present invention (not illustrated). In this embodiment, the surface 86 for applying the patch to the vessel wall is not planar in a manner that permits it to conform generally to the Surface of the vessel. Thus, the surface 86 is provided with a configuration that allows it to generally conform to a portion of the wall of a cylinder which has a radius generally corresponding to the likely radius of the artery to which a patch is to be applied. In an embodiment having a curved surface 86, it has been determined to be preferable to preform the patch 88 so that it maintains a complementary curvature to the surface 86 and the vessel wall.

The patch 88 can be used to seal a puncture site in a viscera or vascular structure by applying the patch 88 and adhesive to the surface of the walls surrounding the perforation to seal the viscera or vascular structure. In order to apply the patch 88 and adhesive over the puncture site, it is desirable to use an applicator which has planar or curved atraumatic delivery surface to deliver the adhesive and the patch 88 to the perforation site.

The patch 88 may be held in place on surface 86 in any of a variety of ways. In one embodiment, the patch 88 includes on its proximal side a light coating of a releasable adhesive, which removably holds the patch 88 on the distal surface 86 of the applicator 80 before application. The net release force required to pull the patch 88 from the patch surface 86 should be low enough to permit the patch 88 to adhere to the vascular wall while permitting the applicator 80 to be separated from the patch 88. This can be accomplished in a variety of ways which will be readily apparent to one of skill in the art, including, for example, appropriate adhesive selection, and optimizing the surface area coverage of the adhesive.

In general, the angle of inclination of patch contact surface 86 conveniently facilitates the use of an oval patch 88. Thus, as illustrated in FIG. 5, an end view of the patch 88 appears circular due to the angle of incline of the patch with respect to the longitudinal axis 68.

In a representative PTCA procedure, the position and axial orientation of a vascular structure, for example, the femoral artery, is determined tactily using three adjacent finger tips. An introduction needle is inserted at about 30° into the artery using finger pressure against the artery upstream of the puncture to stop blood flow.

A short introduction guidewire is passed through the introduction needle and into the artery and the needle is withdrawn leaving the guidewire in position. Next, first and second sheaths, usually an introducer sheath and a dilator sheath, are passed over the guidewire and inserted into the vascular structure as is well known. The dilator sheath is removed leaving the introducer sheath in place to provide arterial access. A guidewire is threaded through the sheath and transluminally to the desired treatment location. Then the balloon catheter or other instrumentation is inserted through the introducer sheath and threaded over the guidewire to a desired location, such as an atherosclerotic plaque.

Once the intravascular procedure has been completed, the catheter is removed. The usual method of hemostasis involves also removing the introducer sheath and guidewire, and applying pressure to the perforation site through the skin until hemostasis has occurred. Alternatively, an obturator may be inserted into the introducer sheath and both obturator and introducer sheath left in place for a period of time, prior to their removal. This additional step depends on the type of procedure and the patient's state of coagulation among other variables.

FIGS. 7–11 schematically illustrate a series of method steps modified with a preferred method of the present invention for inhibiting arterial bleeding at the arterial access site following removal of a diagnostic or treatment catheter. For illustrative purposes, this method will be described as involving the use of the applicator illustrated in FIG. 14; however, it is understood that other types of patch or adhesive applicators can be used as well.

As discussed above, arterial catheterization commonly involves perforating a wall 260 of the vessel 262 such as, for example, the femoral artery, by introducing a needle percutaneously into the vascular structure. Various sheaths, catheters or other instrumentation are introduced through that puncture, as desired, to accomplish the medical procedure. Following the procedure, the guidewire and/or a tubular introduction sheath can be left in the artery to permit the puncture closure method of the present invention.

With reference to FIG. 7, an introducer sheath 250 having a guidewire 252 extending there through is in position within the vascular structure 262. The introducer 250 may have been left in place following the vascular catheterization procedure, or may have been introduced subsequently for the purpose of the present vascular patching procedure.

During catheterization procedures, blood pressure is commonly measured at the arterial access site. As seen in FIG. 7, a pressure sensor display 268 is connected to a side port 266 on the introducer 250.

As illustrated in FIG. 7, the tubular sheath 250 is in one embodiment of the present invention modified by carrying an expander cannula 264 having a introducer cannula 270 slidably mounted thereon. The expander cannula 264 and introducer cannula 270 in this embodiment are mounted on the sheath 250 prior to commencement of the catherization procedure. In this embodiment, the catheterization (e.g. balloon dilatation, drug delivery etc.) is conducted through the sheath 250 having the expander cannula 264 and introducer cannula 270 thereon throughout.

In an alternate embodiment of the invention, the expander cannula 264 is provided in two halves, and adapted to be mounted upon the sheath 250 at the clinical site. If the physician prefers the maneuverability of the sheath 250 without the expander cannula 264 and introducer cannula 270 thereon, he can use a standard sheath 250 for the catherization procedure. At the completion of that procedure, a two or more part expander cannula 264 is reassembled around the introducer sheath 250, and advanced distally along the sheath 250 in accordance with the procedure discussed below. Once the expander cannula 264 is in position against the outer wall of the artery as discussed below, the sheath 250 may be removed, and the distal end of the introducer cannula 270 is advanced over the proximal end of the expander cannula 264 and distally until it is appropriately positioned against the wall of the artery. At that time, the expander cannula 264 can be removed proximally leaving the introducer cannula 270 in place, and ready for the adhesive or adhesive patch application as discussed below.

The split expander cannula of the present invention can be manufactured in a variety of ways, as will be apparent to one of skill in the art. For example, the expander cannula described above and illustrated in FIGS. 15 and 16 can be cut in two halves along an axially extending plane. Preferably, releasable interlocking structures are provided for retaining the two halves in an assembled configuration. For example, pins can be provided on one half of the expander cannula for engaging corresponding recesses on the other half of the cannula. Any of a variety of "snap fit" interlocking structures can be utilized, to accomplish the advantages of the present invention.

Preferably, unlike the embodiment illustrated in FIGS. 15 and 16, the split expander cannula is provided with a substantially uniform outside diameter throughout its entire length. This facilitates mounting the distal end of the introducer cannula over the proximal end of the expander cannula, so that the introducer cannula can be advanced distally along the expander cannula into the appropriate position such as that illustrated in FIG. 10.

Although the split expander cannula described above is described in terms of two opposing halves/the expander may be constructed from any of a variety of pieces which are reassembleable over the sheath into a generally tubular structure. Thus, three or more axially extending segments can be provided for reassembly into a unitary tubular structure. In the preferred embodiment, two halves are provided, which may be snapped fit together at both contact points. Alternatively, the two halves may be joined by an axially extending hinge such as a section of flexible material, so that the hinged expander halves can be positioned around the sheath 250 and then closed thereon to form a tubular expander.

With reference to the embodiment illustrated in FIG. 7, the introducer 250 is withdrawn from the vascular structure 262 to a location where its distal end is adjacent to the ablumenal surface of the vessel wall 260. See FIG. 8. The blood pressure display 268 aids in the proper positioning of the introducer 250 at this location. A surgeon, or like operator, slowly withdraws the introducer 250 from the vessel while monitoring the blood pressure displayed by the blood pressure display 268. The blood pressure significantly drops once the distal end of the introducer 250 is completely withdrawn from the vessel and the perforation shrinks to its nondilated size. In this manner, the operator knows when he or she has withdrawn the distal end of the introducer 250 to a position adjacent to the ablumenal surface of the vessel 262 as illustrated in FIG. 8.

Figure 10:
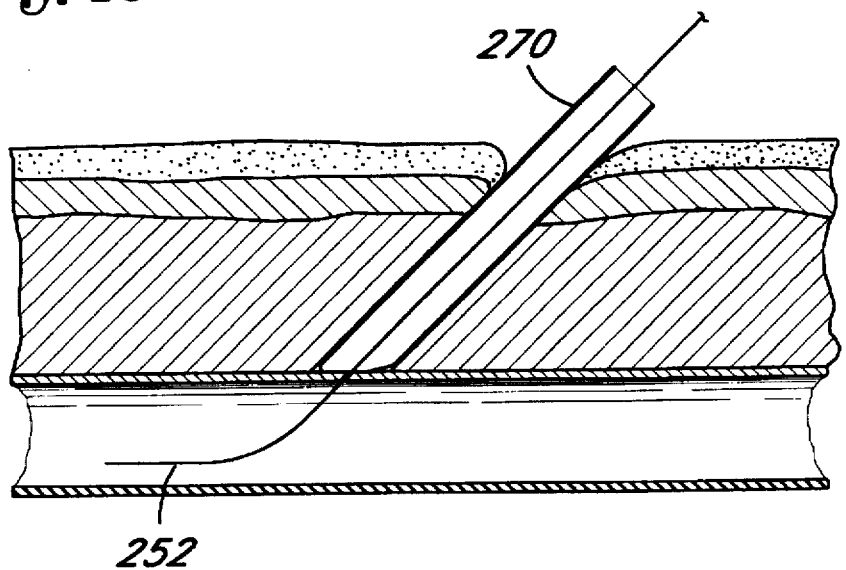
FIG. 10 is a schematic representation as in FIG. 9, with the expander cannula removed.

With reference to FIGS. 8–10, the assembly of the expander cannula 264 and introducer cannula 270 is advanced distally along the catherization sheath 250, until the distal end 265 of the expander cannula 264 contacts the vessel wall. Contact with the vessel wall can be determine by tactile feedback to the operator. Alternatively, indicium such as a line or other marking drawn around the outer circumference of the sheath 250 can be positioned such that it becomes visible to the operator when the expander cannula 264 has been advanced sufficiently distally that the distal end 265 of expander cannula 264 is at the surface of the vessel.

Once the distal end 265 of expander cannula 264 is in position against the exterior wall of the vessel 262, the sheath 264 can be removed to produce the assembly schematically illustrated in FIG. 9. Preferably, the guidewire 252 remains in place.

In the illustrated embodiment, once the introducer cannula 270 is seated against the vessel wall, the expander cannula 264 may be proximally withdrawn, to produce the assembly illustrated schematically in FIG. 10. In an alternate embodiment, the function of the expander cannula 264 and introducer cannula 270 can be combined into a single device. A variety of specific structural modifications can be made, in view of the disclosure herein, by one of ordinary skill in the art in view of the objective to properly positioning the introducer cannula 270 against the vessel wall.

One embodiment of an introducer cannula 270 and dilator cannula 264 is shown in FIGS. 15–18. The cannula 270 has a proximal end 272, a distal end 274, and a minimum inner diameter, which is greater than the maximum diameter of the perforation 276 in the vessel wall 260. The cannula 270 also desirably has a minimum inner diameter, which is greater than the maximum external diameter of the patch applicator 80 This feature allows the applicator 80 to axially, movably fit within the cannula 270.

Preferably, the distal end 274 of cannula 270 is provided with an atraumatic tip 278 to minimize damage to the vessel or surrounding tissue. Distal end 274 is preferably also provided with an angled cut 280 which facilitates placement against the vessel wall at an introduction angle of about 30°.

Preferably, the distal end 274 of the cannula 270 has a sufficient diameter to expose both the perforation 254 and a sufficient area of adjacent vessel wall surrounding the perforation 254 so that a sufficient overlap by the patch can be achieved. For a typical PTCA arterial perforation 254, having a diameter of about 1 mm, an introduction cannula 270 having an inside diameter of about 3 mm and an outside diameter of about 4 mm at its distal end 265 may conveniently be used.

Alternatively, the function of introducer cannula 270 can be readily accomplished by a structure integrally formed or secured to the applicator 80. For example, the delivery surface 86 can be retractably disposed within an outer tubular housing, as will be readily appreciated by one of skill in the art in view of the disclosure herein.

Figure 11:
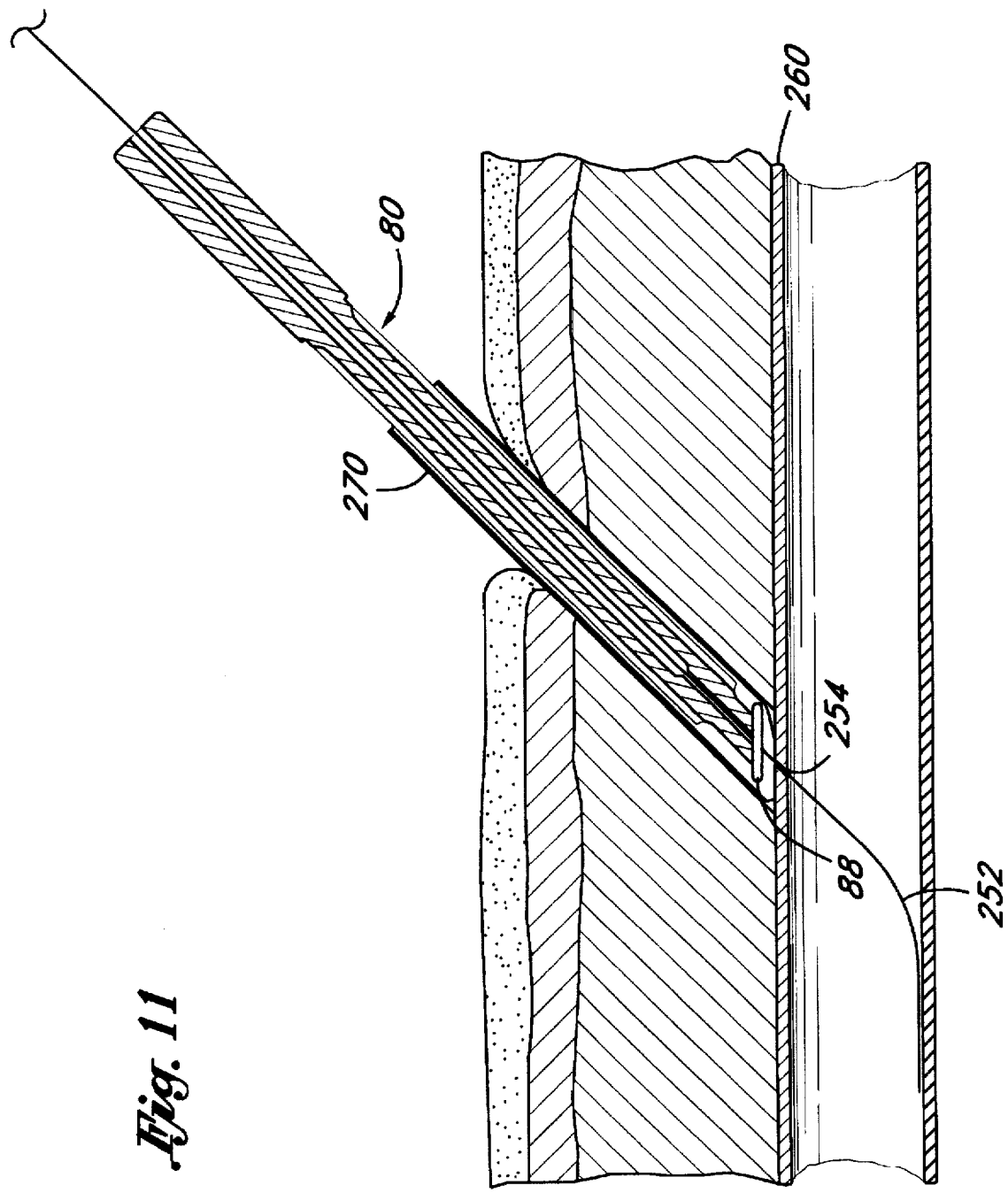
FIG. 11 is a schematic representation as in FIG. 10, with an adhesive patch applicator having a patch thereon advancing down the introducer cannula.

At the point in the procedure illustrated at FIG. 10, the site is prepared for the application of an adhesive patch 88. Patch 88 is preferably secured to a patch applicator 80, as has been previously discussed. Attachment of the patch 88 to the applicator 80 can be accomplished such as through the use of a relatively weak adhesive bond or mechanical interfitting. In one embodiment, the patch 88 is preassembled onto the applicator 80, such as at the point of manufacture, by placing a relatively short shipping guidewire through the patch and into the guidewire lumen of applicator 80. This shipping guidewire may be provided with a distal anchor, such as a T or other configuration, to prevent the patch 88 from advancing off the end of the shipping guidewire. The proximal end of the shipping guidewire extends into the guidewire lumen and possibly out the proximal end of the applicator 80. When ready for use, the shipping guidewire can be removed by gripping the anchor portion or other structure and pulling it from the guidewire lumen. The proximal end of the procedure guidewire 252 is then threaded into the patch 88 and distal end of applicator 80 as illustrated in FIG. 11.

Once a patch 88 is positioned on a patch surface 86 of a patch applicator 80, adhesive can be applied to the patch in any of a variety of ways. In accordance with one aspect of the present invention, the adhesive is applied using an adhesive delivery kit of the type illustrated in FIG. 4. Alternatively, adhesive can be manually applied to the tissue contacting surface of the patch 88 such as by the use of a squeeze tube, dropper, or other structure by the medical personnel at the time of the procedure.

In a typical procedure, the proximal end of a guidewire 252 extends through the perforation and out of the cannula 270. This may be a guidewire inserted for the purpose of the vascular patch procedure, or, more likely is the guidewire which was utilized in the original catherization. The patch applicator 80 having the patch 88 thereon is advanced over the proximal end of the guidewire, and advanced down the guidewire towards the patient. If the adhesive was applied to the patch by way of the automated kit disclosed herein, the patch will contain adhesive at the time it is threaded onto the guidewire. Alternatively, if the adhesive is manually applied to the patch, that application may be accomplished following threading the patch 88 applicator 80 onto the guidewire.

The operator then advances the applicator 80 along the guidewire and through the cannula 270 until the patch 88 contacts the vascular wall 260 without penetrating the perforation 254. See FIG. 11. The operator tactily feels and recognizes when the patch 88 contacts the ablumenal surface of the vessel wall 260.

As an alternative to tactile feedback once the introducer 270 has been properly positioned, the applicator 80 can be provided with visual or mechanical indicia which indicate that the appropriate depth has been reached. For example, applicator 80 can be provided with a mark or line around its circumference indicating the axial depth to which it should be advanced in a distal direction, before the mark disappears within introducer 270. Similarly, the applicator 80 can be advanced distally into the cannula 270 until a physical stop on the applicator 80 reaches the proximal end of the introducer 270.

The operator thereafter withdraws the applicator 80 from the cannula 270 after applying the patch 88 and tissue adhesive. The tissue compresses around the deposited patch 88 and percutaneous perforation. The tissue may be taped or bandaged subsequently to facilitate the physiological healing of the muscular and cutaneous tissue at the access site.

Other embodiments will be readily apparent to those with skill in the art. In all cases, bleeding from the perforation site is preferably controlled by applying external pressure proximal (upstream) to the perforation while applying the adhesive and/or closure device (patch). As described above, the natural elasticity of the vessel wall will normally cause the perforation to shrink, assisting in hemostasis.

As noted above, this method can be used to close any exposed surface which can be reached by any of the above-described applicators. For instance, the above-described applicators may be used in open laparotomy for closing the peritoneal surfaces of various hollow viscera, diaphragm and omentum. The patch 88 applied by the applicator also has the potential of sealing the surface of the liver or spleen, or used to seal perforated lungs, hearts, or pleura. It may also be used to seal a perforation of a vascular lumen, such as an artery or vessel.

In this latter application, the present invention also includes a preferred method for inhibiting arterial bleeding at the arterial access site after percutaneous transluminal procedures, such as, for example, angioplasty, angiography, coronary angiography, atherectomy, or similar procedures.

Although the present invention has been described in terms of certain preferred embodiments, other embodiments can be readily devised by one with skill in the art in view of the foregoing, which will also use the basic concepts of the present invention. Accordingly, the scope of the present invention is to be defined by reference to the following claims.

What is claimed is:

1. An adhesive patch applicator kit, comprising:

a housing having a rotatable cap, said housing having a chamber therein, said cap rotatable about a longitudinal axis of the housing;

an applicator within the chamber, said applicator removably connected to one of the housing or the rotatable cap;

a reservoir in the chamber, said reservoir connected to the other of the housing or the cap;

a tip on the reservoir for expressing adhesive from the reservoir; and an adhesive patch removably attached to the applicator in between the applicator and the tip;

wherein rotation of the cap relative to the housing about the longitudinal axis expresses adhesive from the reservoir through the tip and on to the patch.

2. An adhesive patch applicator kit as in claim 1, wherein the patch is positioned substantially symmetrically about the longitudinal axis and the tip is offset from the longitudinal axis so that rotation of the cap expresses an annular bead of adhesive on the patch.

3. An adhesive patch applicator kit as in claim 1, wherein the adhesive patch is disposed in a plane which is inclined with respect to the longitudinal axis.

4. An adhesive patch applicator kit as in claim 1, further comprising a generally tubular inner housing having a proximal end and a distal end, said tubular inner housing defining said reservoir therein, a movable wall on the tubular inner housing for controllably reducing the volume of the reservoir to express adhesive from the reservoir and along a fluid flow path to the tip, and a valve disposed in the fluid flow path between the reservoir and the tip.

5. An adhesive patch applicator kit as in claim 4, further comprising a spring in the tubular inner housing for biasing the valve in the closed position.

6. An adhesive patch applicator kit as in claim 4, wherein said movable wall comprises a slidable plunger.

7. An adhesive patch applicator kit as in claim 4, further comprising a threaded drive mechanism in said tubular inner housing for converting rotational movement of the cap relative to the housing into axial motion for advancing the movable wall into the reservoir to express adhesive from the reservoir along the fluid flow path to the tip.

8. An adhesive patch applicator kit as in claim 1, wherein said applicator comprises a proximal handle portion and a distal extender portion, wherein the adhesive patch is releasably secured to the distal end of the extender portion.

9. An adhesive patch applicator kit as in claim 8, wherein the distal end of the extender portion comprises an adhesive patch contact surface, and said surface lies generally in a plane which is inclined from a perpendicular to the longitudinal axis.

10. A method of closing a vascular perforation of the type produced during a percutaneous transluminal catheterization procedure, comprising the steps of:

providing an adhesive patch applicator kit of the type having a housing with a first portion that is rotatable with respect to a second portion, said housing having an applicator therein with an adhesive patch on the applicator, said housing further having an adhesive reservoir therein with an applicator tip for expressing adhesive from the reservoir onto the patch;

rotating the first portion of the housing with respect to the second portion of the housing to express an annular bead of adhesive from the reservoir and onto the patch;

removing the applicator having the patch thereon from the housing;

advancing the applicator percutaneously to position the patch against the vascular perforation; and removing the applicator while leaving the patch adhered to the vascular perforation.

* * * * *